(12) United States Patent
Cohen et al.

(10) Patent No.: US 12,144,751 B2
(45) Date of Patent: Nov. 19, 2024

(54) CRIMPING DEVICES FOR PROSTHETIC HEART VALVES

(71) Applicant: Edwards Lifesciences Corporation, Irvine, CA (US)

(72) Inventors: Oren Cohen, Kadima (IL); Ofir Witzman, Kfar Saba (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 230 days.

(21) Appl. No.: 17/577,753

(22) Filed: Jan. 18, 2022

(65) Prior Publication Data

US 2022/0133513 A1    May 5, 2022

Related U.S. Application Data

(63) Continuation of application No. PCT/US2020/042141, filed on Jul. 15, 2020.
(Continued)

(51) Int. Cl.
*A61F 2/95* (2013.01)
*A61F 2/24* (2006.01)
*B23P 11/00* (2006.01)

(52) U.S. Cl.
CPC .......... *A61F 2/9522* (2020.05); *A61F 2/2418* (2013.01); *A61F 2/2436* (2013.01); *B23P 11/005* (2013.01)

(58) Field of Classification Search
CPC ...... B23P 11/005; B25B 27/146; B25B 27/10; Y10T 29/53996; Y10T 29/49913
See application file for complete search history.

(56) References Cited

U.S. PATENT DOCUMENTS 3,409,013 A   11/1968 Berry
3,548,417 A   12/1970 Kisher
(Continued)

FOREIGN PATENT DOCUMENTS

DE    0144167 C    9/1903
DE    2246526 A1   3/1973
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Tyrone V Hall, Jr.
(74) *Attorney, Agent, or Firm* — Klarquist Sparkman, LLP; Sean Seung Kyu Kim

(57) ABSTRACT

A crimping device includes a housing and a crimping band. The housing has a lumen for receiving a prosthetic valve. The crimping band is adjustably coupled to the housing and has a first end portion, a second end portion, and a loop. The loop of the crimping band is disposed within the lumen and move between first and second configurations. In the first configuration, the loop has a first diameter and is configured such that the prosthetic valve in a radially expanded configuration can be positioned radially within the loop. In the second configuration, the loop has a second diameter and is configured to apply a radial force on the prosthetic valve to move the prosthetic valve to a radially compressed configuration. The loop of the crimping band is configured to contact less than half of an axial length of the prosthetic valve.

20 Claims, 9 Drawing Sheets

Related U.S. Application Data

(60) Provisional application No. 62/876,206, filed on Jul. 19, 2019.

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,920,975 A * | 7/1999 | Morales ............ A61F 2/958 606/1 |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpentier |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |

(56) References Cited

U.S. PATENT DOCUMENTS

| | | |
|---|---|---|
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Eidenschink et al. |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,685,055 B2 | 4/2014 | VanTassel et al. |
| 8,747,463 B2 | 6/2014 | Fogarty et al. |
| 9,078,781 B2 | 7/2015 | Ryan et al. |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0040791 A1 | 2/2003 | Oktay |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0137686 A1 | 6/2005 | Salahieh et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0004735 A1 | 1/2010 | Yang et al. |
| 2010/0049313 A1 | 2/2010 | Alon et al. |
| 2010/0082094 A1 | 4/2010 | Quadri et al. |
| 2010/0100176 A1 | 4/2010 | Elizondo et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0030090 A1 | 2/2012 | Johnston et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0152659 A1* | 6/2013 | Maimon ............... B21D 41/00 72/402 |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0135506 A1 | 5/2015 | White |
| 2015/0157455 A1 | 6/2015 | Hoang et al. |
| 2016/0374802 A1 | 12/2016 | Levi et al. |
| 2017/0014229 A1 | 1/2017 | Nguyen-Thien-Nhon et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |
| 2019/0159894 A1 | 5/2019 | Levi et al. |

(56) References Cited

U.S. PATENT DOCUMENTS

| | | |
|---|---|---|
| 2019/0192288 A1 | 6/2019 | Levi et al. |
| 2019/0192289 A1 | 6/2019 | Levi et al. |

FOREIGN PATENT DOCUMENTS

| | | | |
|---|---|---|---|
| DE | 19532846 A1 | 3/1997 | |
| DE | 19546692 A1 | 6/1997 | |
| DE | 19857887 A1 | 7/2000 | |
| DE | 19907646 A1 | 8/2000 | |
| DE | 10049812 A1 | 4/2002 | |
| DE | 10049813 C1 | 4/2002 | |
| DE | 10049814 A1 | 4/2002 | |
| DE | 10049815 A1 | 4/2002 | |
| EP | 0103546 A1 | 3/1984 | |
| EP | 0850607 A1 | 7/1998 | |
| EP | 1057460 A1 | 12/2000 | |
| EP | 1088529 A2 | 4/2001 | |
| EP | 1570809 A1 | 9/2005 | |
| FR | 2788217 A1 | 7/2000 | |
| FR | 2815844 A1 | 5/2002 | |
| GB | 2056023 A | 3/1981 | |
| SU | 1271508 A1 | 11/1986 | |
| WO | 9117720 A1 | 11/1991 | |
| WO | 9217118 A1 | 10/1992 | |
| WO | 9301768 A1 | 2/1993 | |
| WO | 9724080 A1 | 7/1997 | |
| WO | 9829057 A1 | 7/1998 | |
| WO | 9930646 A1 | 6/1999 | |
| WO | 9933414 A1 | 7/1999 | |
| WO | 9940964 A1 | 8/1999 | |
| WO | 9947075 A1 | 9/1999 | |
| WO | 0018333 A1 | 4/2000 | |
| WO | 0041652 A1 | 7/2000 | |
| WO | WO-0121110 A1 * | 3/2001 | ............ A61F 2/958 |
| WO | 0135878 A2 | 5/2001 | |
| WO | 0149213 A2 | 7/2001 | |
| WO | 0154624 A1 | 8/2001 | |
| WO | 0154625 A1 | 8/2001 | |
| WO | 0162189 A1 | 8/2001 | |
| WO | 0047139 A9 | 9/2001 | |
| WO | 0164137 A1 | 9/2001 | |
| WO | 0176510 A2 | 10/2001 | |
| WO | 0222054 | 3/2002 | |
| WO | 0241789 A2 | 5/2002 | |
| WO | 0243620 A1 | 6/2002 | |
| WO | 0247575 A2 | 6/2002 | |
| WO | 0249540 A2 | 6/2002 | |
| WO | 03047468 | 6/2003 | |
| WO | 2005034812 A1 | 4/2005 | |
| WO | 2005055883 A1 | 6/2005 | |
| WO | 2005084595 A1 | 9/2005 | |
| WO | 2006014233 A2 | 2/2006 | |
| WO | 2006032051 A2 | 3/2006 | |
| WO | 2006034008 A2 | 3/2006 | |
| WO | 2006111391 A1 | 10/2006 | |
| WO | 2006127089 A1 | 11/2006 | |
| WO | 2006138173 A2 | 12/2006 | |
| WO | 2005102015 A3 | 4/2007 | |
| WO | 2007047488 A2 | 4/2007 | |
| WO | 2007067942 A1 | 6/2007 | |
| WO | 2007097983 A2 | 8/2007 | |
| WO | 2008005405 A2 | 1/2008 | |
| WO | 2008015257 A2 | 2/2008 | |
| WO | 2008035337 A2 | 3/2008 | |
| WO | 2008091515 A2 | 7/2008 | |
| WO | 2008147964 A1 | 12/2008 | |
| WO | 2008150529 A1 | 12/2008 | |
| WO | 2009033469 A1 | 3/2009 | |
| WO | 2009042196 A2 | 4/2009 | |
| WO | 2009053497 A1 | 4/2009 | |
| WO | 2009061389 A2 | 5/2009 | |
| WO | 2009094188 A2 | 7/2009 | |
| WO | 2009116041 A2 | 9/2009 | |
| WO | 2009149462 A2 | 12/2009 | |
| WO | 2010011699 A2 | 1/2010 | |
| WO | 2010121076 A2 | 10/2010 | |
| WO | 2013106585 A1 | 7/2013 | |
| WO | 2015085218 A1 | 6/2015 | |

OTHER PUBLICATIONS

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

Fontaine, M.D., Arthur B., et al, "Vascular Stent Prototype; Results of Preclinical Evaluation", p. 29-34; Technical Developments and Instrumentation; Jan.-Feb. 1996, vol. 7, No. 1.

Fontaine, M.D., Arthur B., et al, "Prototype Stent: Invivo Swine Studies in the Biliary System1", p. 101-105, Journal of Vascular and Interventional Radiology; Jan.-Feb. 1997; vol. 8, No. 1.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

* cited by examiner

CRIMPING DEVICES FOR PROSTHETIC HEART VALVES

CROSS REFERENCE TO RELATED APPLICATIONS

This application is a continuation of International Application No. PCT/US2020/042141, filed Jul. 15, 2020, which claims the benefit of U.S. Application No. 62/876,206, filed Jul. 19, 2019. The related applications are incorporated by reference herein.

FIELD

This disclosure relates generally to prosthetic heart valves, and more specifically to crimping devices for prosthetic heart valves.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery apparatus and advanced through the patient's vasculature (e.g., through a femoral artery and the aorta) until the prosthetic heart valve reaches the implantation site in the heart. The prosthetic heart valve is then expanded to its functional size. There are various types of expandable prosthetic heart valves, including balloon expandable, self-expandable, and mechanically expandable.

A mechanically expandable prosthetic heart valve can comprise a frame with a plurality of struts that are pivotably connected together. The pivotably-connected struts of the frame can be moved between a radially expanded configuration and a radially compressed configuration by actuating a mechanical actuator that is coupled to the frame.

Due to the unique configuration of mechanically expandable prosthetic heart valves, there is a need for devices and methods configured specifically for mechanically expandable prosthetic heart valves.

SUMMARY

Disclosed herein are devices and methods configured specifically for mechanically expandable prosthetic devices, including prosthetic heart valves and stents. In particular, this disclosure describes various devices and methods configured for crimping mechanically expandable prostheses. The disclosed crimping devices and methods can provide advantages over prior crimping devices and methods, as further described below.

In one representative embodiment, a crimping device comprises a housing and a crimping band. The housing has a lumen configured to receive a prosthetic heart valve. The crimping band is adjustably coupled to the housing and comprises a first end portion, a second end portion, and a loop. The loop of the crimping band is disposed within the lumen of the housing and can be moved between a first configuration and a second configuration. In the first configuration, the loop of the crimping band has a first diameter and is configured such that the prosthetic heart valve in a radially expanded configuration can be positioned radially within the loop. In the second configuration, the loop of the crimping band has a second diameter and is configured to apply a radial force on the prosthetic heart valve to move the prosthetic heart valve from the radially expanded configuration to a radially compressed configuration. The loop of the crimping band is configured to contact less than one half of an axial length of the prosthetic heart valve.

In some embodiments, the loop of the crimping band is configured to contact less than one fourth of the axial length of the prosthetic heart valve.

In some embodiments, the loop of the crimping band is configured to contact less than one eighth of the axial length of the prosthetic heart valve.

In some embodiments, the first end portion of the crimping band is fixed relative to the housing, and the second end portion of the crimping band is movable relative to the housing to move the loop of the crimping band between the first configuration and the second configuration.

In some embodiments, the first and second end portions of the crimping band are movable relative to the housing to move the loop of the crimping band between the first configuration and the second configuration.

In some embodiments, the housing comprises a band opening extending from the lumen of the housing to an outer surface of the housing, wherein in the band opening is configured such that the crimping band can extend therethrough.

In some embodiments, the band opening of the housing comprises an actuation portion and a locking portion. The crimping band can move relative to the housing when the crimping band is radially aligned with the actuation portion of the band opening, and the housing restricts relative movement between the crimping band and the housing when the crimping band is radially aligned with the locking portion of the band opening.

In some embodiments, the crimping device further comprises a locking mechanism coupled to the housing and configured to restrict relative movement between the crimping band and the housing.

In some embodiments, the locking mechanism is disposed adjacent to the band opening of the housing.

In some embodiments, the locking mechanism comprises a plurality of jaws, and the jaws are movable between on open configuration spaced from the crimping band and a closed configuration contacting the crimping band.

In some embodiments, the jaws comprise mating features configured to retain the jaws in the closed configuration.

In some embodiments, the mating features of the jaws comprise interlocking tabs that extend from the jaws.

In some embodiments, the crimping band comprises an indicator configured to signify to a user that the prosthetic heart valve is fully radially compressed.

In some embodiments, the crimping device further comprises one or more stopper elements extending outwardly from the crimping band, and the stopper elements are configured to restrict relative movement between the crimping band and the housing.

In some embodiments, the crimping band has only one loop.

In another representative embodiment, a crimping device for a mechanically expandable prosthetic heart valve comprises a housing and a crimping band. The housing comprises a base and a main body. The main body extends from the base and comprises a lumen configured to receive a mechanically expandable prosthetic heart valve. The main body further comprising a first opening and a second opening. The first opening and the second opening are spaced apart and extend from an inner surface of the main body that defines the lumen to an outer surface of the main body. The crimping band comprises a first end portion, a second end portion, and only a single loop disposed between the first and second end portions. The loop of the crimping band comprises a width that is less than an axial length of the mechanically expandable prosthetic heart valve.

In some embodiments, the crimping band is a flexible polymeric band.

In some embodiments, the crimping band is a flexible suture.

In some embodiments, the crimping band is a flexible wire.

In another representative embodiment, a method of crimping an implantable device is provided. The method comprises positioning the implantable device within an loop of a crimping band with the implantable device in a radially expanded state. The method further comprises tensioning the crimping band such that a diameter of the loop decreases, contacts a first portion of the implantable device, and moves the implantable device to a radially compressed configuration. The crimping band is configured to apply a radially compressive force to the implantable device when the crimping band is tensioned. The first portion of the implantable device comprises less than one half of an axial length of the implantable device.

In some embodiments, the method further comprises advancing a capsule of a delivery apparatus over a second portion of the implantable device while crimping band is tensioned. The second portion comprises less than one half of an axial length of the implantable device.

In some embodiments, the method further comprises slackening the crimping band and advancing the capsule of the delivery apparatus over the first portion of the implantable device and a third portion of the implantable device. The first portion, the second portion, and the third portion of the implantable device together comprise the axial length of the implantable device.

The various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the disclosure will become more apparent from the following detailed description, claims, and accompanying figures.

DETAILED DESCRIPTION

General Considerations

Figure 1:
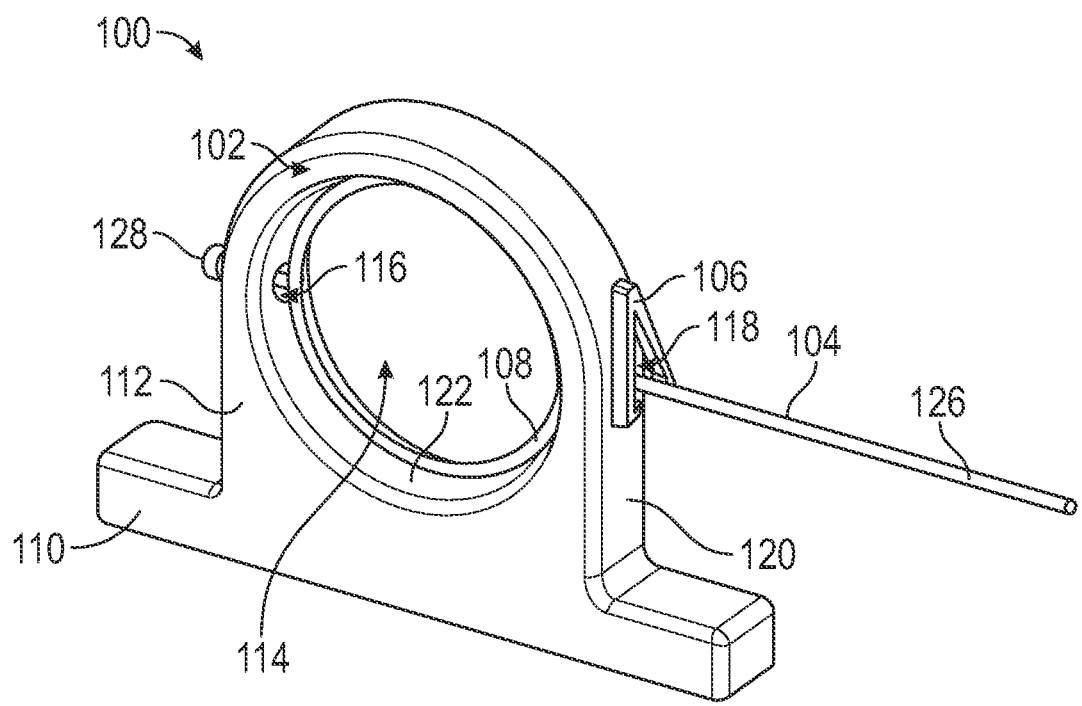
FIG. 1 is a perspective view of an exemplary crimping device.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

EXEMPLARY EMBODIMENTS

Disclosed herein are devices and methods configured specifically for mechanically expandable prosthetic heart valves, though the disclosed devices and methods may in some instances be used with other types of prosthetic heart valves (e.g., balloon expandable and/or self-expandable prosthetic heart valves) or other prostheses (e.g., stents). In particular, this disclosure describes various devices and methods configured for radially compressing ("crimping") mechanically expandable prosthetic heart valves.

The disclosed devices and methods are configured to take advantage of and/or utilize crimping behavior of certain valves, such as mechanically expandable prosthetic heart valves, which can uniformly collapse/crimp as a result of local crimping force applied to the prosthetic heart valve. In other words, the devices and methods disclosed herein can be particularly advantageous for crimping a prosthetic heart valve in which collapsing a section of the valve results in the collapsing of the entire prosthetic heart valve.

Accordingly, the disclosed crimping devices and methods can provide advantages over prior crimping devices and methods, particularly when used with mechanically expandable prosthetic heart valves. For example, the disclosed crimping devices are quick and easy to use. The disclosed crimping devices are also simple, safe, and less expensive to produce than typical crimping devices because they have relatively fewer moving parts/mechanisms. Additional features and advantages are described below.

FIG. 1 shows a crimping device 100, according to one embodiment. The crimping device 100 can comprise two main components: a housing 102 and a crimping band 104. In some embodiments, the crimping device 100 can also include a locking mechanism 106. The housing 102 can be configured to support the crimping band 104 and/or the locking mechanism 106. The crimping band 104 can form a loop 108 and can be moved relative to the housing 102 and the locking mechanism 106 to adjust the size of the loop 108, in a lasso-like manner. The locking mechanism 106 can selectively secure the crimping band 104 relative to the housing 102, and thereby secure the loop 108 at a desired configuration. As such, the crimping device 100 can, for example, be used to radially compress or crimp a mechanically expandable prosthetic heart valve from a radially expanded configuration (e.g., a functional configuration) to a radially compressed configuration (e.g., a delivery configuration), as shown in FIGS. 5-12. Additional details regarding the crimping device 100 and methods of using the crimping device 100 to crimp a prosthetic heart valve are provided below.

Referring again to FIG. 1, the housing 102 of the crimping device 100 can comprise a base 110 and a main body 112. The base 110 of the housing 102 can be configured to support and/or stabilize the crimping device 100. The main body 112 extend from the base 110 and can be configured to support the crimping band 104 and to receive a prosthetic heart valve.

The base 110 of the housing 102 can, in some instances, be configured to engage a table or bench. In some embodiments, the base 110 can comprise one or more mounting features configured such that the housing 102 can be mounted to a table. For example, the mounting features can include openings, slots, etc. configured to receive fasteners (e.g., bolts, screws, etc.), which can coupled the housing 102 to the table. In some embodiments, one or more surfaces of the base 110 can comprise friction elements (e.g., polymeric pads and/or coatings) configured to enhance frictional engagement between the base 110 and a surface on which the base 110 is disposed (e.g., a table).

Figure 6:
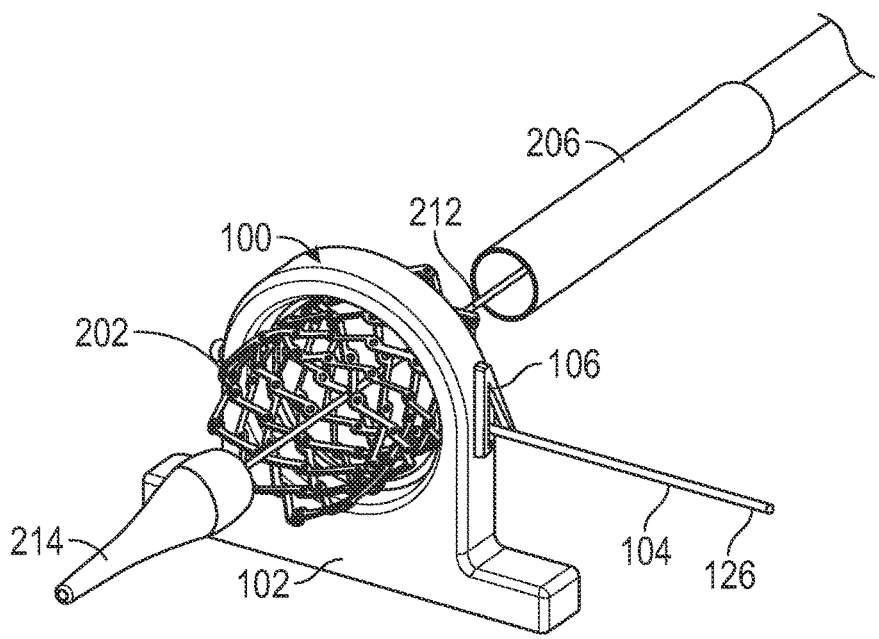
FIG. 6 is a perspective view of the crimping device of FIG. 1 and the delivery assembly of FIG. 5, showing the prosthetic heart valve in a radially expanded configuration and disposed radially within the crimping device.

The main body 112 of the housing 102 can comprise a lumen 114 configured to receive a prosthetic heart valve and/or a delivery apparatus (see, e.g., FIG. 6). The main body 112 can also comprise one or more openings configured for receiving the crimping band 104. For example, in the illustrated embodiment, the main body 112 comprises a first opening 116 and a second opening 118. The first and second openings 116, 118 can extend from an outer surface 120 of the main body 112 to the inner surface 122 of the main body 112, which defines the lumen 114.

The first and second openings 116, 118 in the main body 112 can be spaced circumferentially around the lumen 114 relative to each other. For example, in some embodiments, the first and second openings 116, 118 are directly opposite each other relative to the main body 112 (e.g., 180 degree apart). In other embodiments, the first and second openings 116, 118 can be spaced circumferentially relative to each other by about 90-180 degrees. In certain embodiments, the first and second openings 116, 118 can be spaced circumferentially relative to each other by about 135-180 degrees.

Although not shown, in some embodiments, the main body 112 can also comprise a groove or recess formed in the inner surface 122. The groove can be configured to at least partially receive the loop 108 of the crimping band 104 to selectively retain the loop 108 of the crimping band 104 against the inner surface 122 of the main body 112 (e.g., when positioning a prosthetic heart valve within the lumen 114).

In the illustrated embodiment, the outer surface 120 of the main body 112 comprises a generally U-shape such that the main body 112 comprises a generally annular shape. In other embodiments, the outer surface 120 of the main body 112 can comprise various other shapes (e.g., rectangular, triangular, etc.)

The housing 102 can be formed of various materials such as polymers, metals, composites, etc.

Figure 2:
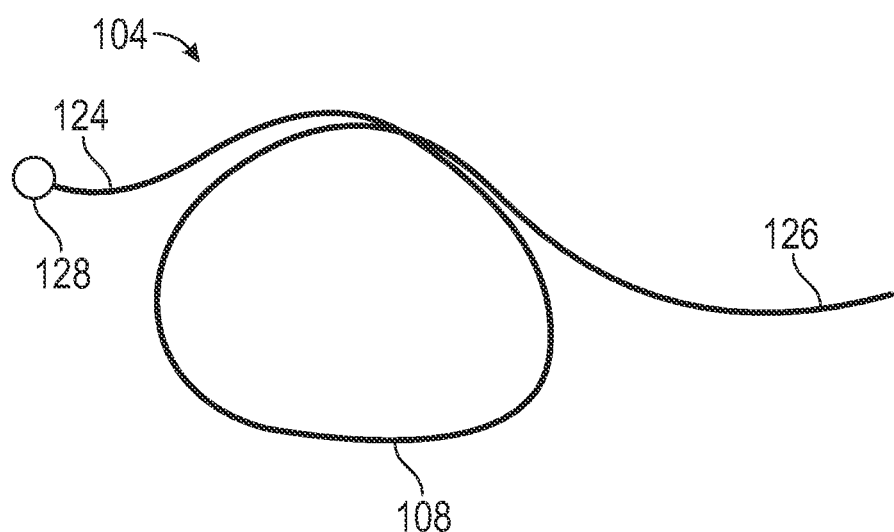
FIG. 2 is a perspective view of a crimping band of the crimping device of FIG. 1.

Referring to FIG. 2, the crimping band 104 of the crimping device 100 can comprise a first end portion 124 and a second end portion 126. As mentioned above, the crimping band 104 can be arranged to form the loop 108 between the first and second end portions 124, 126. In some instances, the crimping band 104 have only one loop. In other instances, the crimping band 104 can comprise a plurality of loops (e.g., 2-5). In some embodiments, the loop 108 can formed by coiling the crimping band 104 in a helical manner. In other embodiments, the loop 108 can be formed by tying a knot (e.g., an overhand knot) in the crimping band 104.

Referring to FIG. 1, the crimping band 104 can be coupled to the housing 102 such that the first end portion 124 of the crimping band 104 extends through the first opening 116 of the housing 102, the loop 108 of the crimping band 104 is disposed within the lumen 114 of the housing 102, and the second end portion 126 of the crimping band 104 extends through the second opening 118 of the housing 102. The crimping band 104 can be tensioned or slackened to adjust the diameter of the loop 108.

The crimping band 104 and the first and second openings 116, 118 of the housing 102 can be configured such that the crimping band 104 can be moved relative to the first and second openings 116, 118 of the housing 102. As such, the diameter of the loop 108 of the crimping band 104 can be adjusted by tensioning or slackening the crimping band 104. In some embodiments, both the first and second end portions 124, 126 of the crimping band 104 can be moved relative to the housing 102. In such embodiments, the crimping band 104 can be tensioned by moving both the first and second end portions 124, 126 away from each other (e.g., by pulling on the end portions). In other embodiments, one end portion (e.g., the first end portion 124) of the crimping band 104 can remain stationary relative to the housing 102, and the other end portion (e.g., the second end portion 126) of the crimping band 104 can be moved relative to the housing 102, as shown in the illustrated embodiment. In such embodiments, the crimping band 104 can be tensioned by moving the free end of the crimping band away from the stationary end of the crimping band 104.

The tension of the crimping band 104 can be adjusted manually and/or automatically. For example, in some embodiments, the crimping band 104 can be tensioned and/or slacked by manually tensioning/slackening the crimping band 104 by hand. In other embodiments, the crimping band 104 can be adjusted automatically, such as by coupling the crimping band 104 (and/or a spool) to an electric motor. In such embodiments, the crimping device 100 can further comprise one or more actuators (e.g., buttons, switches, etc.) configured to actuate the electric motor.

In some embodiments, an end portion of the crimping band 104 can be secured relative to the housing 102. For example, an end portion of the crimping band 104 can be secured to the housing 102 with adhesive and/or fasteners. As another example, an end portion of the crimping band 104 can be integrally formed with (e.g., co-molded) with the housing 102. As yet another example, the crimping band 104 can have a stopper element disposed thereon and/or coupled thereto configured to restrict movement between the crimping band 104 and the housing 102. In the illustrated embodiment, the crimping band 104 has a stopper element 128 disposed on the first end portion 124 of the crimping band 104. The stopper element 128 can be larger than the first opening 116 of the housing 102 so that the first end portion 124 of the crimping band 104 cannot "pull through" the first opening 124 when tension is applied to the crimping band 104 (e.g., when the second end portion 126 of the crimping band 104 is pulled away from the housing 102.

In the illustrated embodiment, the stopper element 128 comprises a flange that is integrally formed with and extends radially outwardly from the main portion of the crimping band 104. In other embodiments, the stopper element can be a knot that is formed in the crimping band 104. In yet other embodiments, the stopper element can be a ferrule, cap, and/or other member that is coupled (e.g., clamped) to the end portion of the crimping band 104.

The crimping band 104 can be a flexible element such as a band, cord, wire, suture, etc. The crimping band 104 can be formed of various materials. For example, the crimping band 104 can be formed of polymer (e.g., nylon, polyethylene (PE), ultra-high-molecular-weight polyethylene (UHMWPE) (e.g., Dyneema® fibers), etc.) and/or metal (e.g., stainless steel, nitinol, titanium, etc.).

In the illustrated embodiment, the crimping band 104 has a generally circular cross-sectional profile taken in a plane perpendicular a longitudinal axis of the crimping band 104. In other embodiments, the crimping band 104 can have various other cross-sectional profiles (e.g., rectangular, ovular, etc.).

Figure 3:
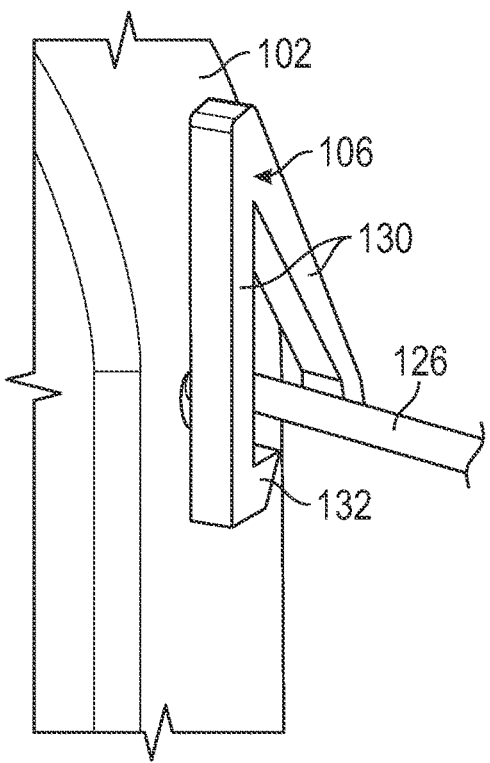
FIG. 3 is a detail view of a locking mechanism of the crimping device of FIG. 1, showing the locking mechanism in an unlocked configuration.
Figure 4:
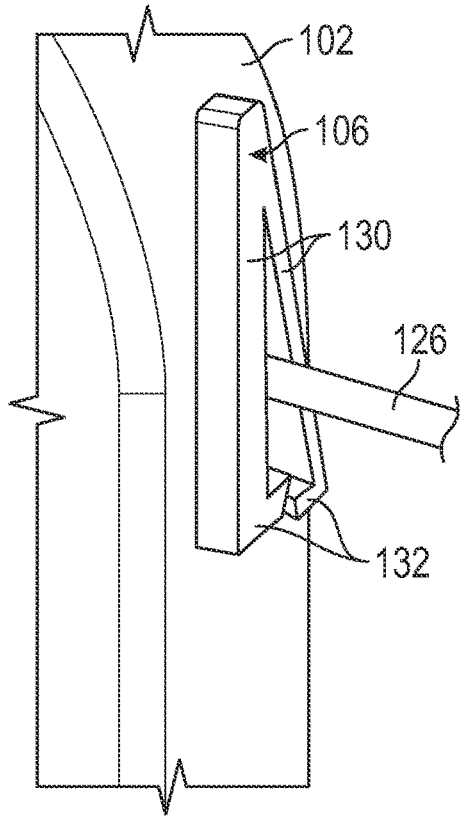
FIG. 4 is a detail view of the locking mechanism of the crimping device of FIG. 1, showing the locking mechanism in a locked configuration.

Referring to FIG. 1, the locking mechanism 106 of the crimping device 100 can be coupled to the housing 102. Turning to FIGS. 3-4, the locking mechanism 106 can be moved between an unlocked configuration (FIG. 3) and a locked configuration (FIG. 4) to selectively restrict relative movement between the crimping band 104 and the locking mechanism 106 (and the housing 102). As such, the locking mechanism 106 can be used to selectively retain the crimping band 104 in a desired configuration (e.g., a particular diameter and/or a tensioned/slackened state).

The locking mechanism 106 can comprise a pair of jaws 130. The jaws 130 of the locking mechanism 106 can be pivotably coupled together such that the jaws 130 can be moved between an open state (e.g., FIG. 3) and a closed state (e.g., FIG. 4). In the open state, the jaws 130 of the locking mechanism 106 are spaced apart from the crimping band 104 such that the crimping band 104 can be moved relative to the jaws 130 and the housing 102. Therefore, with the jaws 130 in the open state, the second end portion 126 of the crimping band 104 can be moved relative to the locking mechanism 106 and the housing 102 to adjust the diameter of the loop 108 of the crimping band 104. In the closed state, the jaws 130 of the locking mechanism 106 engage the second end portion 126 of the crimping band 104 and thereby restrict relative movement between the crimping band 104, the locking mechanism 106, and the housing 102 such that the diameter of the loop 108 of the crimping band 104 is fixed.

In some embodiments, the jaws 130 of the locking mechanism 106 can have mating features 132. The mating features 132 can be configured to engage one another so that the jaws can be releasably secured in the closed state, as shown in FIG. 4. For example, the mating features 132 of the jaws 130 can include tabs that are configured to overlap and engage with one another (e.g., similar to the locking features of a hemostat).

In some embodiments, one or more of the jaws 130 of the locking mechanism 106 can comprise a recess configured to receive at a portion of the crimping band 104. The recess can be configured to improve the frictional engagement between the jaws 130 and the crimping band 104 by increasing the surface area of the jaws that contacts the crimping band 104. In certain embodiments, the recess can comprise a semi-circular cross-sectional profile taken in a plane perpendicular to the longitudinal axis of the crimping band 104.

In lieu of or in addition to the recess, the jaws 130 of the locking mechanism 106 can comprise one or more friction increasing elements or coatings. For example, the jaws 130 can comprise projections (e.g., ribs) and/or texturing (e.g., non-smooth) configured to increase frictional engagement between the jaws 130 and the crimping band 104. Additionally or alternatively, the jaws 130 can comprise a coating that increases frictional engagement between the jaws 130 and the crimping band 104.

In the illustrated embodiment, the crimping device 100 comprises only one locking mechanism 106, which is disposed adjacent to the second opening 118 of the housing 102 and configured to engage the second end portion 126 of the crimping band 104. In other embodiments, the locking mechanism 106 can be disposed adjacent to the first opening 116. In yet other embodiments, the crimping device 100 can comprise more than one (e.g., two) locking mechanisms. For example, the crimping device can comprise a locking mechanism disposed adjacent to each opening of the housing and configured to engage a respective end portion of the crimping band.

The crimping device 100 can be used, for example, to crimp a prosthetic heart valve from a radially expanded configuration to a radially compressed configuration. The prosthetic heart valve can be releasably coupled to a delivery apparatus configured for implanting the prosthetic heart valve. For example, FIGS. 5-12 depict the crimping device 100 being used with a delivery assembly 200, which comprises a prosthetic heart valve 202 and a delivery apparatus 204. The crimping device 100 can be used to radially compress the prosthetic heart valve 202 and to retain the prosthetic heart valve 202 in the radially compressed state while the prosthetic heart valve 202 is loaded into a capsule 206 of the delivery apparatus 204. Additional details of an exemplary crimping procedure and the delivery assembly 200 are provided below.

Figure 5:
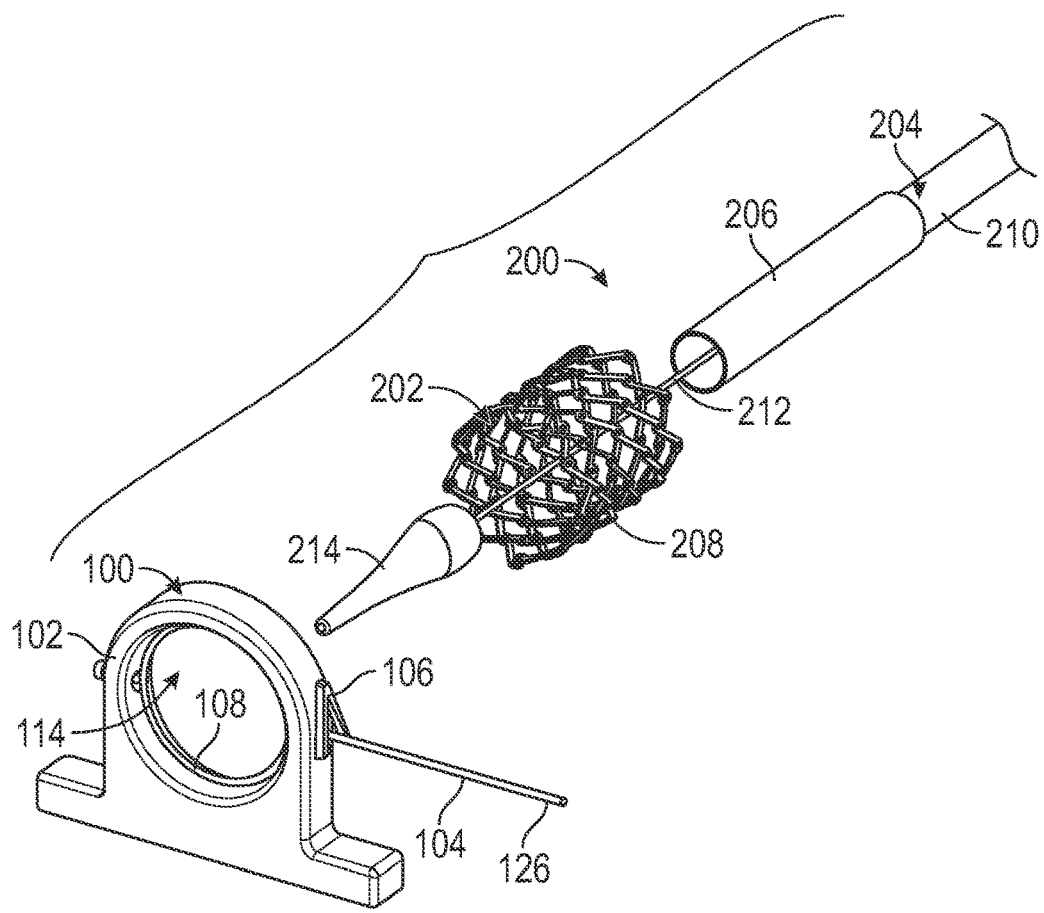
FIG. 5 is a perspective view of the crimping device of FIG. 1 and an exemplary delivery assembly, the delivery assembly comprising a prosthetic heart valve and a delivery apparatus.

Referring to FIG. 5, the prosthetic heart valve 202 of the delivery assembly 200 can comprise a frame 208 and a valve structure (not shown for purposes of illustration). The frame 208 of the prosthetic heart valve 202 can have a plurality of struts that are pivotably coupled together. As such, the frame 208 of the prosthetic heart valve 202 can be moved between a radially expanded and axially foreshortened configuration (e.g., FIG. 5) and a radially compressed and axially elongate configuration (e.g., FIG. 7) by applying forces (e.g., radial and/or axial) to the prosthetic heart valve 202. The prosthetic heart valve 202 may be referred to as a mechanically expandable prosthetic heart valve.

Since the struts of the frame of the prosthetic heart valve 202 can pivot relative to each other, the force needed to radially compress the prosthetic heart valve 202 (and/or other mechanically expandable prosthetic heart valves) is relatively less than the force required to radially compress typical self-expanding and balloon expandable prosthetic heart valves.

Although not shown, the prosthetic heart valve 202 can also comprise one or more mechanical actuators configured to apply forces to the frame 208 and/or to lock the frame 208 in a desired configuration. Additional details regarding exemplary mechanically expandable prosthetic valves can be found, for example, in U.S. Pat. No. 10,603,165, U.S. Publication Nos. 2018/0311039, 2018/0344456, and 2019/0060057, and International Publication No. WO 2020/081893, which are incorporated by reference herein.

Referring still to FIG. 5, the delivery apparatus 204 of the delivery assembly 200 can comprise a first shaft 210 (which can also be referred to as "the outer shaft 210"), a second shaft 212 (which can also be referred to as "the inner shaft 212), and a nosecone 214. The outer shaft 210 can comprise the capsule 206 (which can also be referred to as "a sheath") disposed at the distal end portion of the outer shaft 210 and configured to receive and retain a radially compressed prosthetic heart valve therein. The inner shaft 212 can extend through the outer shaft 210. The nosecone 214 can be coupled to a distal end portion of the inner shaft 212. The inner and outer shafts 210, 212, can be moved relative to each other. Although not shown, the delivery apparatus 204 can comprise one or more other components, including one or more additional shafts configured for releasably coupling the prosthetic heart valve 202 to the delivery apparatus 204 and/or one or more handles coupled to the shafts 210, 212. Further details regarding delivery apparatus and coupling a prosthetic heart valve to a delivery apparatus can be found, for example, in U.S. Pat. No. 10,603,165 and U.S. Publication Nos. 2018/0311039 and 2019/0060057.

To prepare the delivery apparatus 204 to receive the prosthetic heart valve 202, the inner shaft 212 of the delivery apparatus 204 can be positioned relative to the outer shaft 210 such that the nosecone 214 is disposed distal to the distal end of the capsule 206, as shown in FIG. 5. The prosthetic heart valve 202 can be positioned over the nosecone 214 and the inner shaft 212 such that the prosthetic heart valve 202 is axially disposed between the nosecone 214 and the distal end of the capsule 206.

Although not shown, the prosthetic heart valve can be releasably coupled to the delivery apparatus. This can be accomplished, for example, by releasably coupling an actuation shaft of the delivery apparatus to one or more actuators of the prosthetic heart valve.

Referring to FIG. 6, the delivery assembly 200 be positioned relative to the crimping device 100 such that the nosecone 214 and the distal end of the inner shaft 212 extend through the lumen 114 (FIG. 5) of the crimping device 100 and the prosthetic heart valve 202 is disposed within the lumen 114 of the crimping device 100.

As shown in FIG. 6, the crimping device 100 can be configured such that the crimping band 104 axially overlaps and contacts only a portion of the axial length of the prosthetic heart valve 202. As used herein, the axial length of the prosthetic heart valve is the length of the frame of the prosthetic heart valve as measured from the inflow end of the frame to the outflow end of the frame when the frame is in a fully expanded, functional configuration. In some embodiments, the crimping band 104 can axially overlap and contact less than one half of the axial length of the prosthetic heart valve 202. In certain embodiments, the crimping band 104 can axially overlap and contact less than one fourth of the axial length of the prosthetic heart valve 202. In particular embodiments, the crimping band 104 can axially and contact with less than one eighth of the axial length of the prosthetic heart valve 202. This is significantly different than typical crimping devices, which have crimping elements (e.g., jaws) configured to axially overlap and contact the entire (or at least most of the) length of the prosthetic heart valve. The crimping band 104 of the crimping device 100 can be relatively narrow because the crimping device 100 is configured to take advantage of the low crimping forces needed to compress the mechanically expandable prosthetic heart valve 202, and thus can compress the entire prosthetic heart valve by contacting only a relatively small portion of the prosthetic heart valve.

Figure 7:
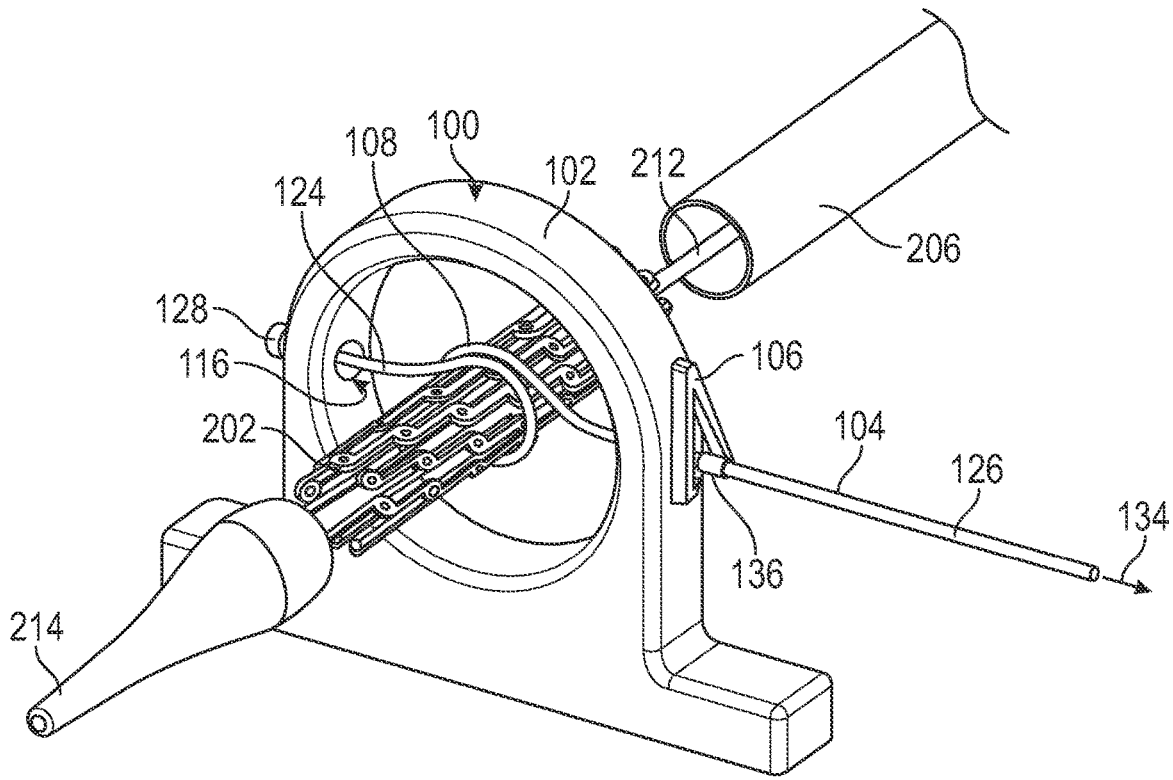
FIG. 7 is a perspective view of the crimping device of FIG. 1 and the delivery assembly of FIG. 5, showing the prosthetic heart valve disposed radially within the crimping device and in a radially compressed configuration.

With the prosthetic heart valve disposed within the crimping device 100, the prosthetic heart valve 202 can be radially compressed by tensioning the crimping band 104, as shown in FIG. 7. This can be accomplished by pulling the second end portion 126 of the crimping band 104 away from the housing 102. As a result, the loop 108 of the crimping band 104 radially contracts and applies a radially compressive force to a portion of the frame 208 of the prosthetic heart valve 202, which causes the struts of the frame 208 to pivot relative to each other, which causes the entire frame 208 to radially compress due to the pivoting connections between the struts of the frame 208.

Also, due to the pivoting struts of the prosthetic heart valve 202, the amount of force needed to compress the prosthetic heart valve 202 is relatively low. Accordingly, a user can supply the force necessary to radially compress the prosthetic heart valve 202 by simply grasping the second end portion 126 of the crimping band 104 with their hand and pulling the crimping band 104 away from the housing 102 (e.g., in the direction of arrow 134). Thus, the crimping device 100 can be relatively simple and easy to use compared to typical crimping devices, which can require complex mechanisms and/or require the user to apply large forces to radially compress a prosthetic heart valve.

In some embodiments, the crimping device 100 can comprise one or more indicators configured to provide a user with information about or a status of the crimping of the prosthetic heart valve. An indicator can, for example, be configured to signify to a user that the prosthetic heart valve is fully radially compressed. As shown in FIG. 7, the crimping band 104 comprises an indicator 136. The indicator 136 can be markings, coloration, symbols, and/or any other type of visual indicia.

The indicator 136 can be positioned relative to the crimping band 104 such that the indicator 136 is disposed within the housing 102 (e.g., adjacent the inner surface 122 of the housing 102) when the loop 108 of the crimping band 104 (and thus the prosthetic heart valve) is in the radially expanded configuration (e.g., FIG. 6) and such that the indicator 136 is disposed outside of the housing 102 (e.g., adjacent the locking mechanism 106) when the loop 108 of the crimping band 104 (and thus the prosthetic heart valve) is in a pre-determined radially compressed configuration (e.g., FIG. 7). In this manner, the indicator 136 can inform the user that the prosthetic heart valve is fully crimped, which can in help prevent the prosthetic heart valve from being over crimped.

Additionally or alternatively, the crimping device 100 can comprise a stopper element (not shown) coupled to the crimping band. The stopper element can be configured to allow relative movement between the crimping band 104 and the housing 102 to a pre-determined point and to restrict relative movement between the crimping band 104 and the housing 102 beyond the pre-determined point. The stopper element can be radially larger than the second opening 118 of the housing 102. As such, the stopper element can be disposed within the lumen 114 of the housing 102 when the loop 108 of the crimping band 104 is in radially expanded configuration (e.g., FIG. 6). As the crimping band 104 is tensioned and the loop 108 contracts, the stopper element can move toward the second opening 118 of the housing 102. When the crimping band 104 reaches the pre-determined point, the stopper element can contact the inner surface 122 of the housing 102 adjacent to the second opening 118 and thereby prevent the crimping band 104 from moving further relative to the housing 102. In some embodiments, the stopper element can be a knot or other radial projection that is an integral part of the crimping band. In other embodiments, the stopper element can a separate element (e.g., a ferrule or a cable stop) that is coupled to the crimping band 104.

Figure 8:
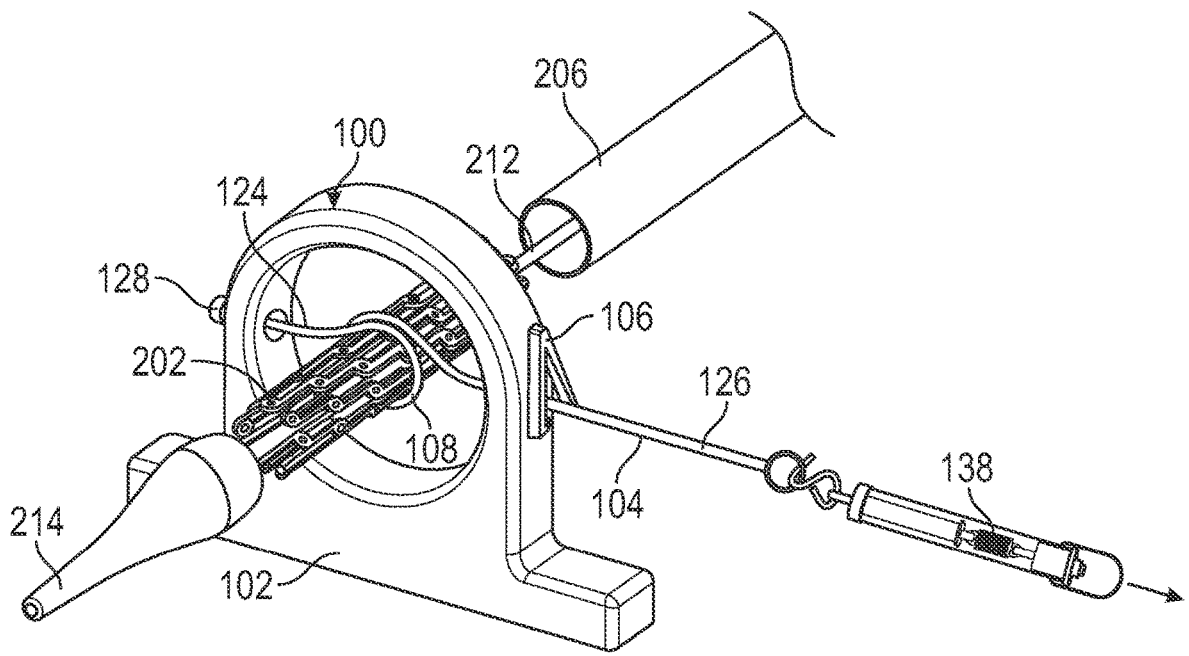
FIG. 8 is a perspective view of a force control mechanism, the crimping device of FIG. 1, and the delivery assembly of FIG. 5, showing the force control mechanism coupled to the crimping device.

In lieu of or in addition to the indicator 136 and/or the stopper element, the crimping device 100 can further comprise a force control mechanism. The force control mechanism can be configured to limit and/or indicate the force applied to the crimping band 104. For example, as shown in FIG. 8, the crimping device 100 can comprise a spring load gauge 138 (which can also be referred to as "a spring scale") coupled to the second end portion 126 of the crimping band 104. The spring load gauge 138 can provide a readout of the amount of force applied to the crimping band 104 (e.g., in pounds and/or newtons). In other embodiments, a force control mechanism can take the form of a crimping band that is formed of an elastic material configured to elongate (i.e., elastically deform) once the force on the crimping band reaches a certain magnitude. In such embodiments, the user could pull on the crimping band 104 until the crimping band 104 begins to elongate, at which point the user would know the prosthetic heart valve was fully crimped and thus stop pulling on the crimping band 104.

In embodiments comprising an electric motor configured to adjust the tension of the crimping band 104, the crimping device 100 can comprise one or more force (e.g., torque) limiting mechanisms configured to limit the force that the crimping band can apply to a prosthetic heart valve. For example, the crimping device 100 can comprise a slip clutch and/or electronic circuitry configured to limit the electrical current to the motor.

Figure 9:
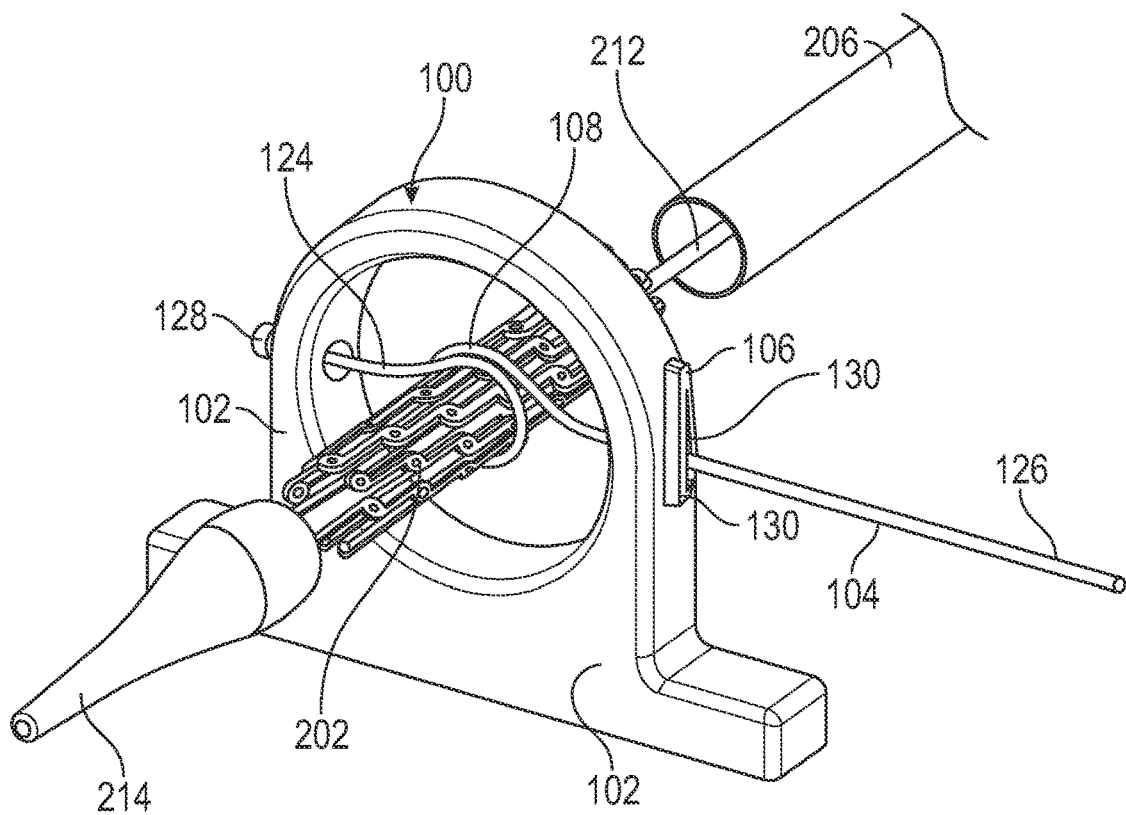
FIG. 9 is a perspective view of the crimping device of FIG. 1 and the delivery assembly of FIG. 5, showing the prosthetic heart valve retained in the radially compressed configuration by the locking mechanism of the crimping device.

Once the prosthetic heart valve is crimped to a desired radially compressed configuration, the locking mechanism can be used to retain the prosthetic heart valve 202 in the crimped configuration. The locking mechanism 106 can be actuated by moving the jaws 130 of the locking mechanism 106 into contact with the crimping band 104, as shown in FIG. 9. As such, the jaws 130 can restrict relative movement between the crimping band 104 and the housing 102. This retains the loop 108 of the crimping band 104 in contact with the prosthetic heart valve 202, and thereby retains the prosthetic heart valve 202 in the radially compressed configuration.

Figure 10:
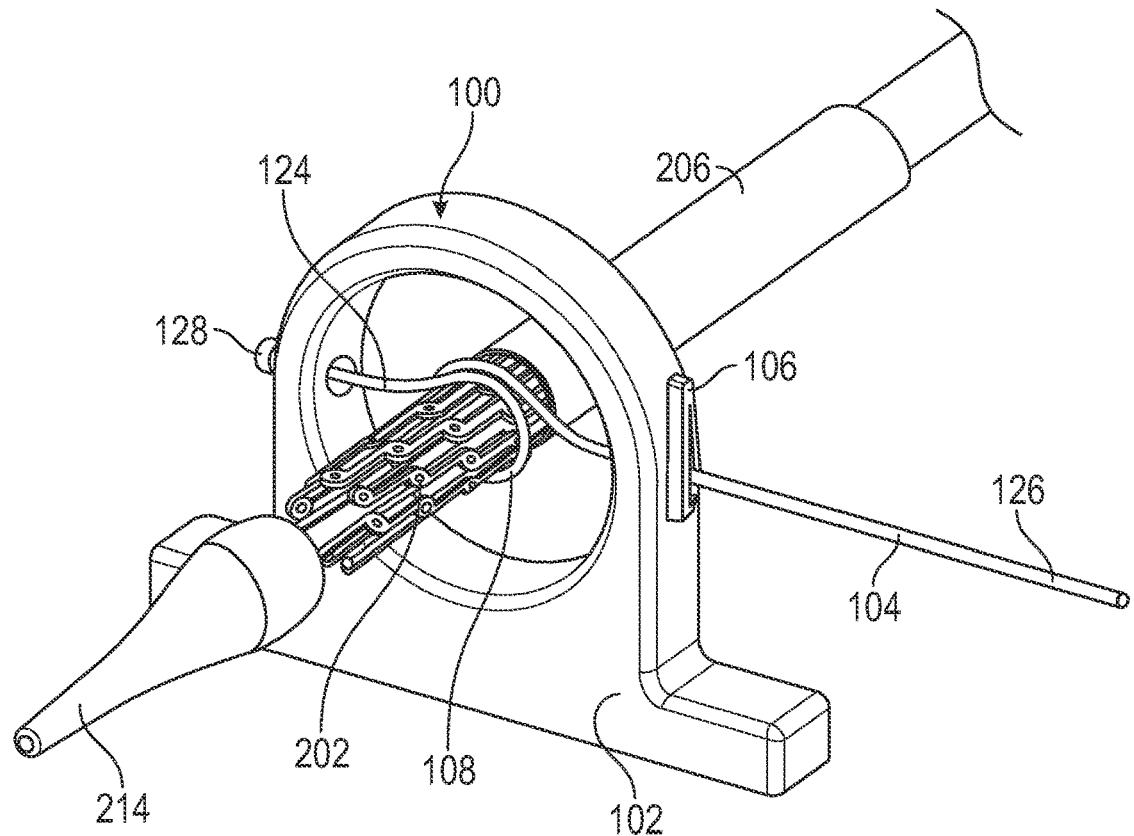
FIG. 10 is a perspective view of the crimping device of FIG. 1 and the delivery assembly of FIG. 5, showing the prosthetic heart valve retained in the radially compressed configuration by the locking mechanism of the crimping device and a capsule of the delivery apparatus.

When in the radially compressed configuration, the prosthetic heart valve 202 can be loaded into the capsule 206 of the delivery apparatus 204. This can be accomplished by moving the outer shaft 210 of the delivery apparatus 204 axially relative to the prosthetic heart valve 202 such that the capsule 206 extends radially over the proximal end portion of the prosthetic heart valve 202, as shown in FIG. 10. The outer shaft 210 can be moved axially relative to the prosthetic heart valve 202 until the distal end of the capsule 206 is disposed adjacent to the crimping band 104.

Figure 11:
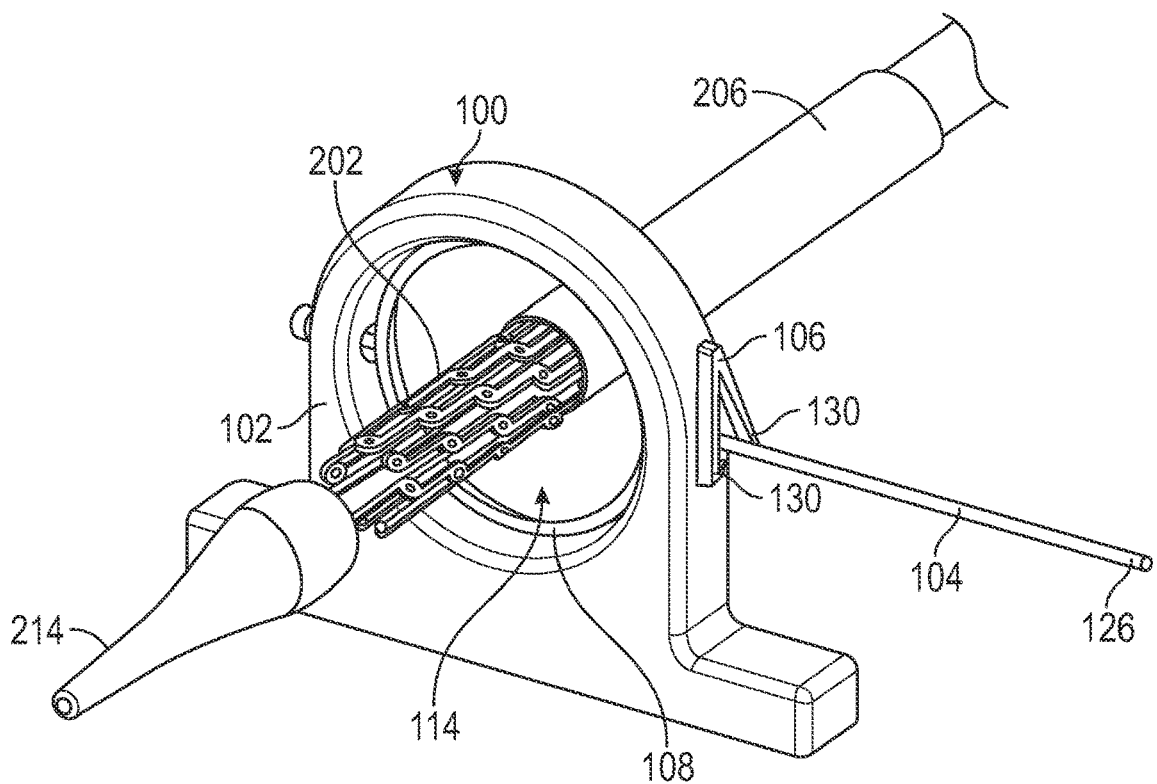
FIG. 11 is a perspective view of the crimping device of FIG. 1 and the delivery assembly of FIG. 5, showing the prosthetic heart valve retained in the radially compressed configuration by the capsule of the delivery apparatus and released from the crimping device.

Even though the capsule 206 is disposed over only a portion of the prosthetic heart valve 202, the capsule 206 of the delivery apparatus 204 can then be used to retain the prosthetic heart valve 202 in the radially compressed configuration while the prosthetic heart valve 202 is released from the crimping device 100. To release the prosthetic heart valve 202, the locking mechanism 106 can be unlocked by opening the jaws 130, and the crimping band 104 can be radially expanded so as to be radially spaced from the prosthetic heart valve 202, as shown in FIG. 11.

Figure 12:
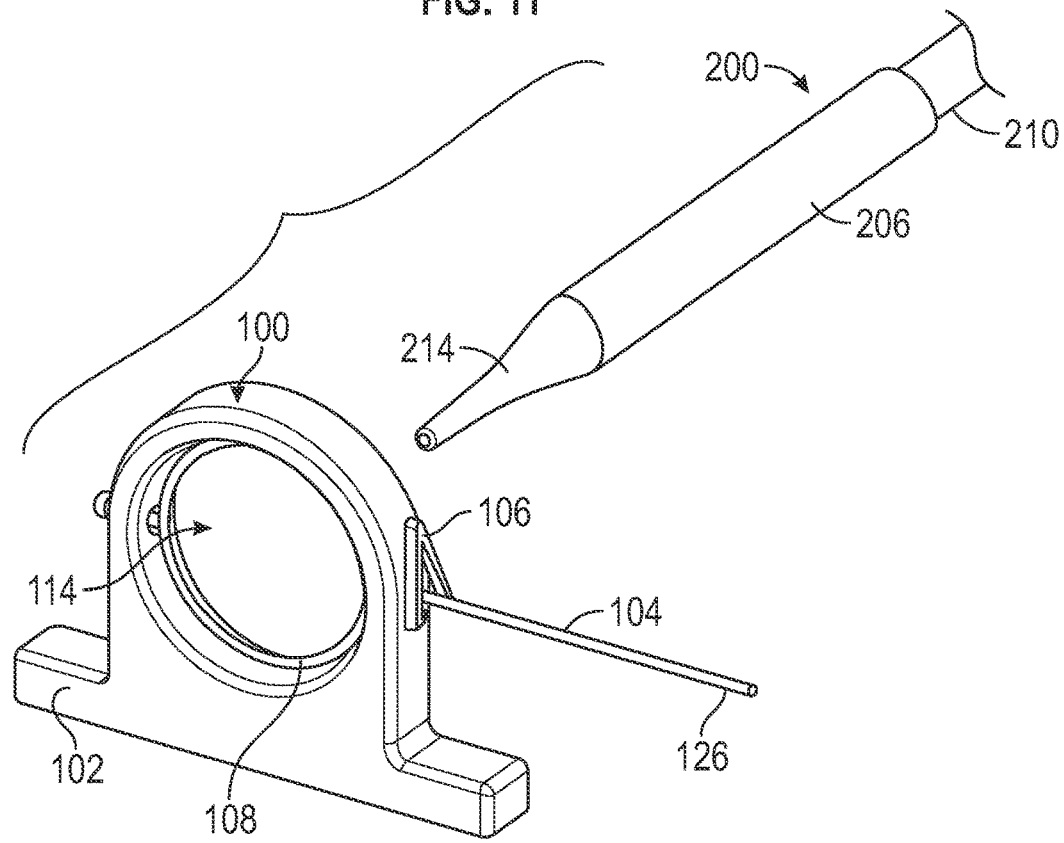
FIG. 12 is a perspective view of the crimping device of FIG. 1 and the delivery assembly of FIG. 5, showing the prosthetic heart valve fully loaded into the capsule of the delivery apparatus.

As shown in FIG. 12, the capsule 206 of the delivery apparatus 204 can then be moved axially relative to the prosthetic heart valve 202 so that the capsule 206 extends over the entire prosthetic heart valve 202. The shafts 210, 212 can be moved relative to each other such that the nosecone 214 and the capsule 206 contact each other, and the delivery assembly 200 can be withdrawn from the lumen 114 of the crimping device 100.

The delivery assembly 200 can then be inserted into a patient's vasculature, and the delivery apparatus 204 can be used to deliver the prosthetic heart valve 202 to a desired implantation location (e.g., a native aortic annulus).

Figure 13:
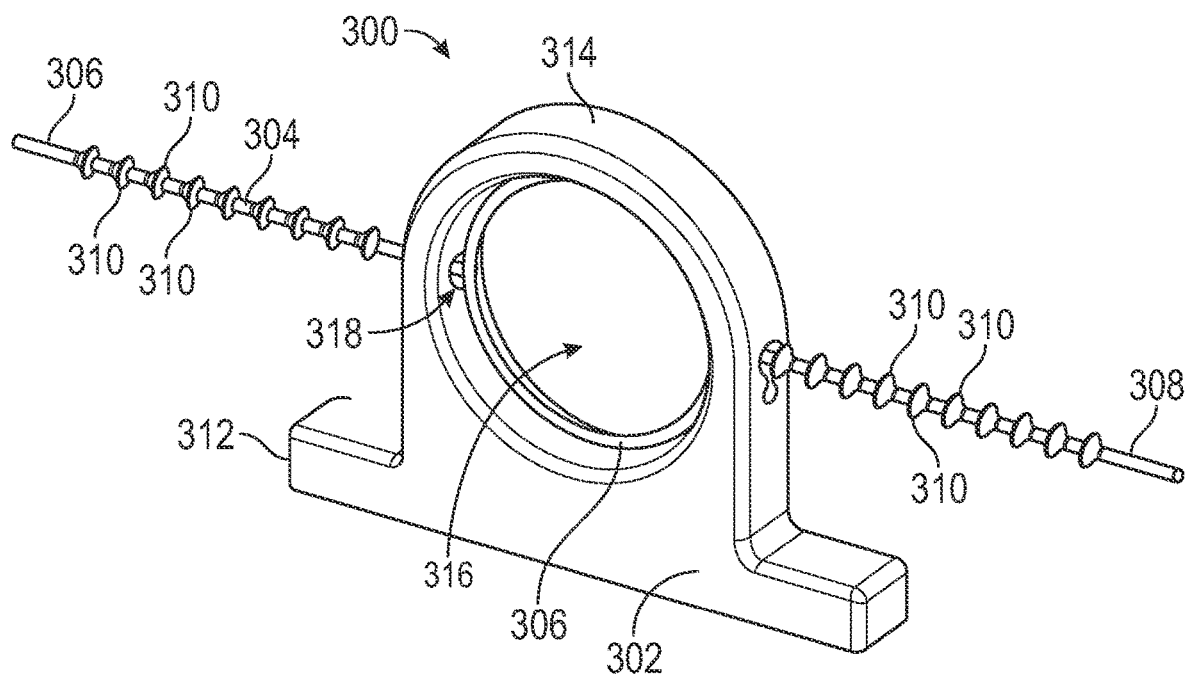
FIG. 13 is a perspective view of another exemplary crimping device, showing a crimping band in a slackened state.
Figure 14:
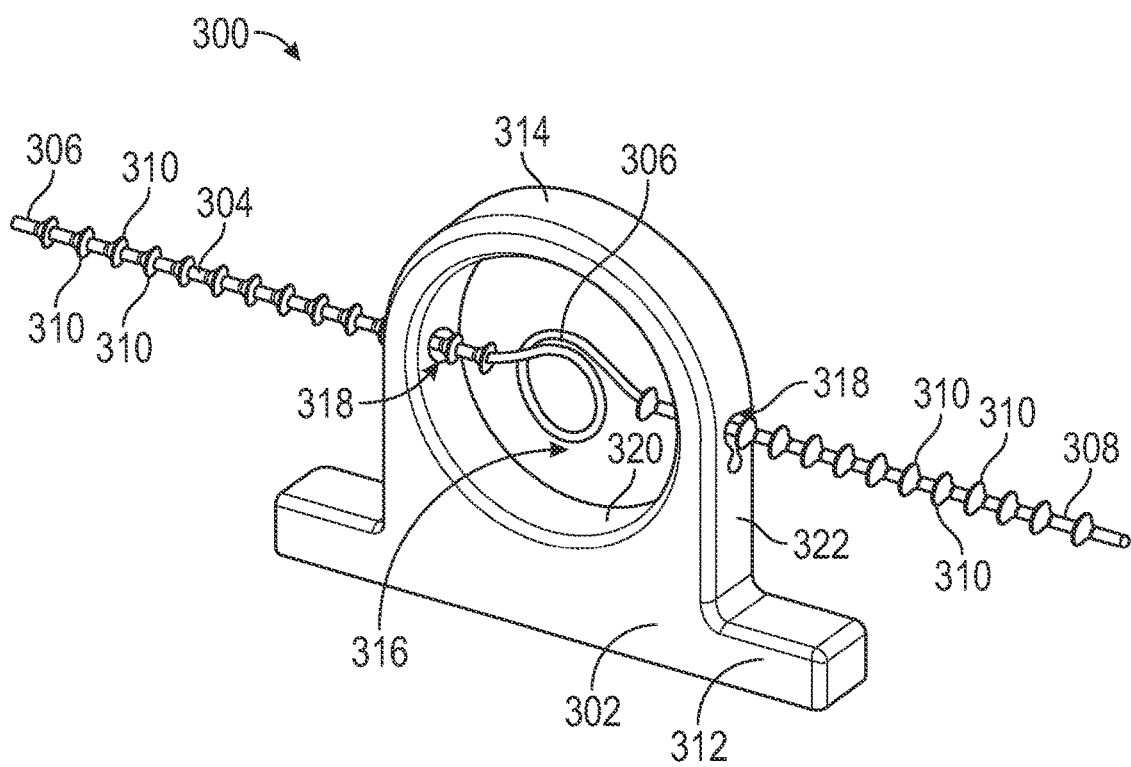
FIG. 14 is a perspective view of the crimping device of FIG. 13, showing a crimping band in a tensioned state.
Figure 15:
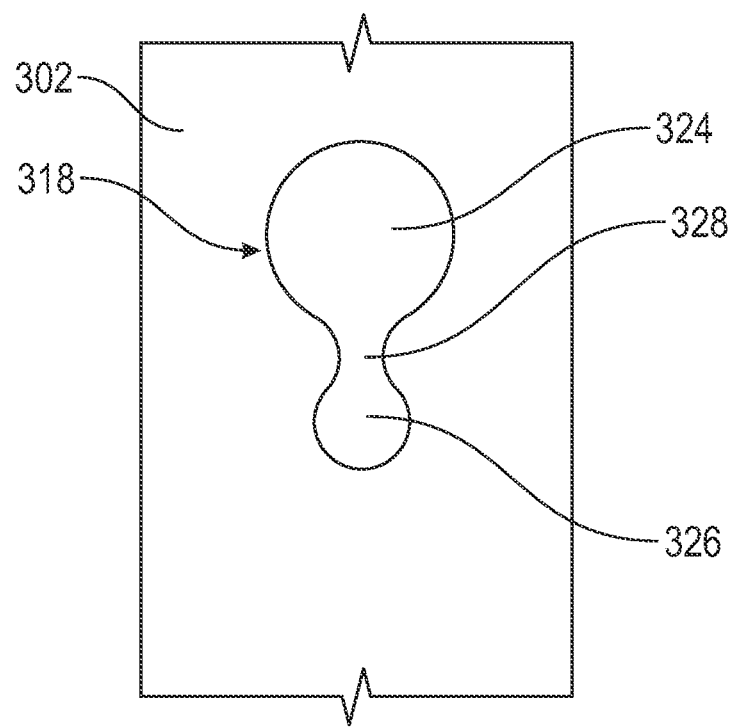
FIG. 15 is a detail side view of the housing of the crimping device of FIG. 13.
Figure 16:
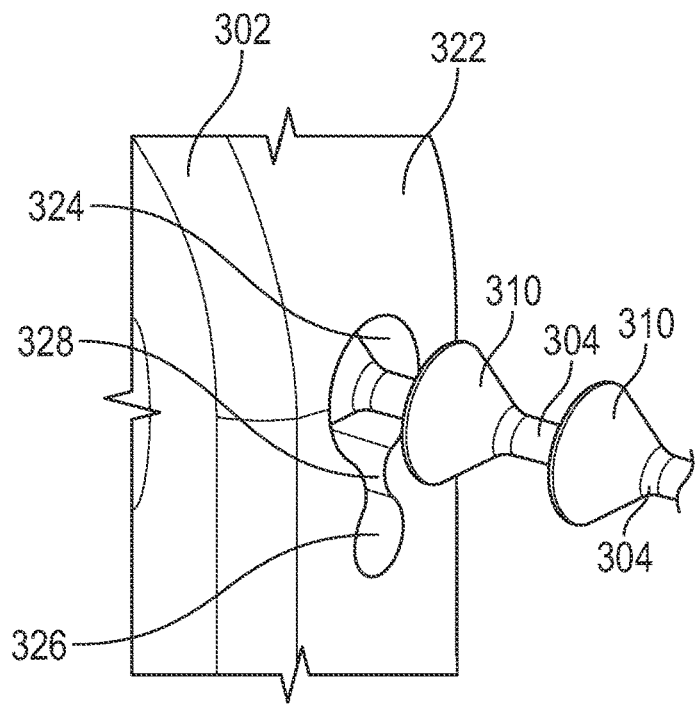
FIG. 16 is a detail perspective view of the crimping device of FIG. 13, showing the crimping band in an unlocked configuration.
Figure 17:
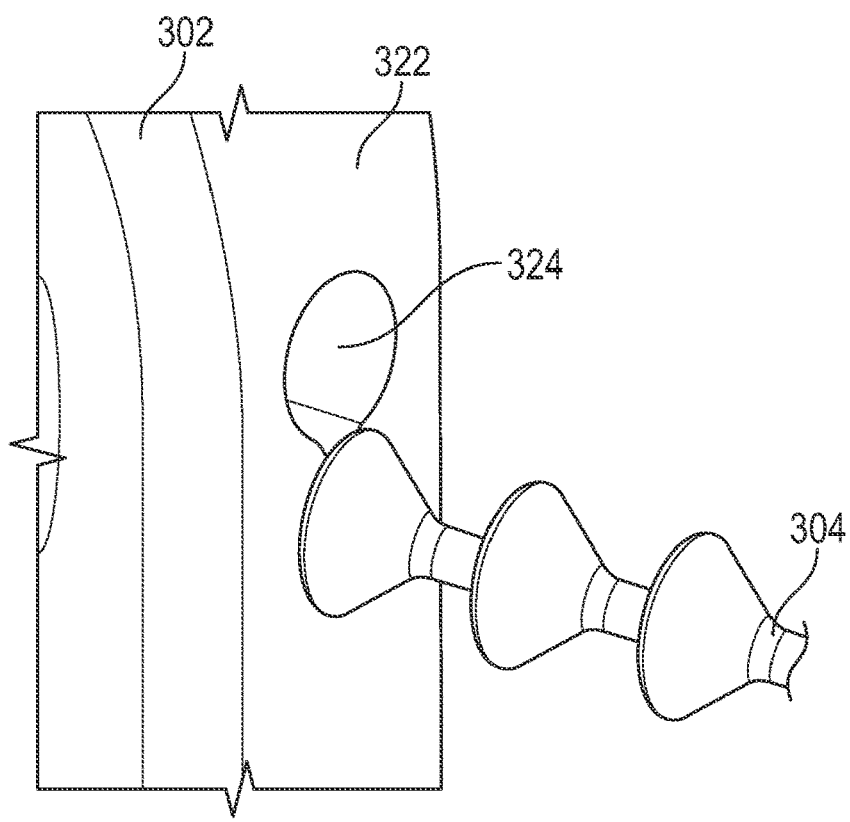
FIG. 17 is a detail perspective view of the crimping device of FIG. 13, showing the crimping band in a locked configuration.

FIGS. 13-14 show a crimping device 300, according to another embodiment. Generally speaking, the crimping device 300 is similar to the crimping device 100 in that the crimping device 300 comprises a housing 302 and a crimping band 304 with an adjustable loop 306 that function similar to the housing 102, the crimping band 104, and the loop 108 of the crimping device 100, respectively. The crimping device 300 differs from the crimping device 100 in several ways. For example, the crimping band 304 of the crimping device 300 is configured such that both end portions 308 of the crimping band 304 can be moved relative to the housing 302; whereas, the crimping band 104 is configured such that only the second end portion 126 of the crimping band 104 can be moved relative to the housing 102 (e.g., during normal operation). The crimping band 304 also comprises a plurality of stopper elements 310 disposed along its length; whereas the crimping band 104 has a substantially uniform diameter along its length. Also, as shown in FIGS. 15-17, the crimping device 300 comprises a locking mechanism that is integrally formed in the housing 302; whereas the crimping device has a separate locking mechanism 106 that is coupled to the housing 102. Additional details regarding the crimping device 300 and its components are provided below.

Referring to FIGS. 13-14, the housing 302 of the crimping device 300 comprises a base 312 and a main body 314. The main body 314 includes a lumen 316 configured such that a delivery assembly can be inserted therethrough (see, e.g., FIGS. 6-7). The main body 314 also includes band openings 318 extending from an interior surface 320 (which defines the lumen 316) of the main body 314 to an exterior surface 322 of the main body 314. The band openings 318 can be circumferentially spaced apart from each other and configured to receive the crimping band 304.

It should be noted that the loop 306 of the crimping band 304 is shown as having a circular shape for purposes of illustration; however, when a prosthetic heart valve is not disposed within the loop 306 and the crimping band 304 is tensioned, the loop 306 would disappear (or become knotted) and the crimping band 304 would be substantially flat.

Turning now to FIG. 15, each band opening 318 can comprise an actuation portion 324, a locking portion 326, and a connection portion 328 disposed between the actuation portion 324 and the locking portion 326. The actuation portion 324 can be larger (e.g., radially) than the locking portion 326 and the connection portion 328. In some embodiments, the locking portion 326 can be larger than the connection portion 328. In other embodiments, the locking portion 326 and the connection portion 328 can be the same size.

As shown in FIG. 16, the actuation portion 324 of the band opening 318 can be configured such that the stopper elements 310 of the crimping band 304 can pass therethrough. Thus, the crimping band 304 can be aligned with the actuation portions 324 of the band openings 318 when the crimping band 304 is being moved relative to the housing 302.

As shown in FIG. 17, the locking portion 326 and the connection portion 328 of the band opening 318 can be configured such that the main portion of the crimping band 304 (i.e., the portion(s) between the stopper elements 310) can pass therethrough and such that the stopper elements 310 of the crimping band 304 cannot pass therethrough. Thus, once the crimping band is adjust relative to the housing 302 to a desired diameter by moving the crimping band 304 through the actuation portions 324 of the band openings 318, the crimping band 304 can be moved from the actuation portions 324 of the band openings 318, through the connection portions 328 of the band openings 318, and into the locking portions 326 of the band openings 318. In this "locked" configuration, the stopper elements 310 of the crimping band 304 can engage the exterior surface 322 of the housing 302 adjacent to the band openings 318, and thereby restrict relative movement between the crimping band 304 and the housing 302.

In some embodiments, the stopper elements can be evenly spaced relative to each other. In other embodiments, the stopper elements can be non-evenly spaced. For example, the stopper elements disposed towards the ends of the crimping band can be spaced further apart from adjacent stopper elements than the stopper elements that are disposed on the middle portion of the crimping band.

The stopper elements 310 of the crimping band 304 can extend radially outwardly from the main portion of the crimping band 304. For example, in the illustrated embodiment, the stopper elements 310 have a frustoconical shape that extends radially outwardly from the crimping band 304. In certain embodiments, as shown, the smaller radial portion of each stopper element can be disposed closer to an adjacent end portion than the larger radial portion. This configuration allows the crimping band 304 to move relatively more easily in one direction than the other. Specifically, the "directional" configuration allows the crimping band 304 can pass more easily through the band openings 318 when moving from the interior surface 320 to the exterior surface 322 of the housing 302 than when moving from the from the exterior surface 322 to the interior surface 320 of the housing 302. In some instances, the stopper elements 310 can be configured such that the end portions 308 of the crimping band 304 can move away from the housing 302 when the crimping band 304 is aligned with the locking portions 326 of band openings 318 (e.g., when tensioning the crimping band) and such that the end portions 308 cannot move toward the housing 302 when the crimping band 304 is aligned with the locking portions 326 of band openings 318 (e.g., when slackening the crimping band). In other words, the diameter of the loop 306 of the crimping band 304 can be reduced but cannot be expanded when the stopper elements 310 are aligned with the locking portions 326 of the band openings 318.

In other embodiments, the stopper elements can comprise various other shapes. For example, the stopper elements can comprise tabs or legs that project outwardly, such as in a T-shape or V-shape taken in a plane parallel to the longitudinal axis of the crimping band. In some such embodiments, the band openings can comprise a rectangular cross-sectional profile, which allows the stopper elements of the crimping band to pass through the band openings when the stopper elements of the crimping band are in a first orientation (e.g., vertical) that aligns the tabs with the major axis of the rectangular opening, and which restricts movement of the stopper elements of the crimping band relative to the housing when the stopper elements of the crimping band are in a second orientation (e.g., horizontal) that aligns the tabs with the minor axis of the rectangle such that the tabs contact the exterior surface of the housing. In this manner, the crimping band can be moved between the locked and unlocked states by rotating (e.g., twisting) the crimping band (e.g., by 90 degrees) relative to the housing.

The crimping device 300 can be used to crimp a mechanically expandable prosthetic heart valve (e.g., the prosthetic heart valve 202). A radially expanded prosthetic heart valve and an end portion of a delivery apparatus can be inserted into the lumen 316 of the housing 302 when the loop 306 of the crimping band 304 is in the radially expanded configuration (e.g., FIG. 13). The diameter of the loop 306 of the crimping band 304 can then be reduced by aligning the end portions 308 of the crimping band 304 with the actuation portions 324 of the band openings 318 of the housing 302 (see, e.g., FIG. 16) and moving the end portions 308 of the crimping band 304 away from the housing 302. This results in the loop 306 of the crimping band contacting the prosthetic heart valve and applying a radially inward force on the prosthetic heart valve.

The prosthetic heart valve can be retained in the radially compressed state by moving the crimping band 304 relative to the housing 302 from the actuation portions 324 of the band openings 318, through the connection portions 328 of the band openings 318, and into the locking portions 326 of the band openings 318, as shown in FIG. 17. As such, the stopper elements 310 of the crimping band 304 contact the exterior surface 322 of the housing 302 and thereby restricts relative movement (e.g., at least slackening) between the crimping band 304 and the housing 302.

The prosthetic heart valve can be partially loaded into a capsule of a delivery apparatus. The capsule of the delivery apparatus can retain the prosthetic heart valve in the radially compressed configuration, and the crimping device 300 can be released from the prosthetic heart valve. To release the prosthetic heart valve, the crimping band 304 can be moved relative to the housing 302 so that the stopper elements 310 radially align with the actuation portions 324 of the band openings 318. The crimping band 304 can be slackened such that the diameter of the loop 306 of the crimping band 304 increases. The prosthetic heart valve and the delivery apparatus can be retracted from within the loop 306 and the capsule of the delivery apparatus can be advanced over the rest of the prosthetic heart valve, or vice versa.

The crimping devices described herein are quick and simple to use and less expensive to produce compared to typical crimping devices that often have complicated mechanisms.

It should be noted that, although the disclosed crimping devices described as primarily for use with prosthetic heart valves, the disclosed crimping devices can also be used with other implantable devices (e.g., stents).

The features described herein with regard to any example can be combined with other features described in any one or more of the other examples, unless otherwise stated. For example, one or more features of the crimping device 100 can be combined with the one or more features of the crimping device 300. In particular, the crimping band 304 can be used with the crimping device 100 in lieu of the crimping band 104.

In view of the many possible embodiments to which the principles of the disclosure may be applied, it should be recognized that the illustrated embodiments are only preferred examples and should not be taken as limiting the scope of the claims. Rather, the scope of the claimed subject matter is defined by the following claims and their equivalents.

The invention claimed is:

1. A crimping device comprising:
   a housing having a lumen configured to receive a prosthetic heart valve; and
   a crimping band adjustably coupled to the housing and comprising a first end portion, a second end portion, and a loop, wherein the loop of the crimping band is disposed within the lumen of the housing and can be moved between a first configuration and a second configuration, wherein in the first configuration, the loop of the crimping band has a first diameter and is configured such that the prosthetic heart valve in a radially expanded configuration can be positioned radially within the loop, wherein in the second configuration, the loop of the crimping band has a second diameter and is configured to apply a radial force on the prosthetic heart valve to move the prosthetic heart valve from the radially expanded configuration to a radially compressed configuration, and wherein the loop of the crimping band is configured to contact less than one half of an axial length of the prosthetic heart valve,
   wherein the housing comprises a band opening extending from the lumen of the housing to an outer surface of the housing, wherein in the band opening is configured such that the crimping band can extend therethrough.

2. The crimping device of claim 1, wherein the loop of the crimping band is configured to contact less than one fourth of the axial length of the prosthetic heart valve.

3. The crimping device of claim 1, wherein the loop of the crimping band is configured to contact less than one eighth of the axial length of the prosthetic heart valve.

4. The crimping device of claim 1, wherein the first end portion of the crimping band is fixed relative to the housing, and wherein the second end portion of the crimping band is movable relative to the housing to move the loop of the crimping band between the first configuration and the second configuration.

5. The crimping device of claim 1, wherein the first and second end portions of the crimping band are movable relative to the housing to move the loop of the crimping band between the first configuration and the second configuration.

6. The crimping device of claim 1, wherein the band opening of the housing comprises an actuation portion and a locking portion, wherein the crimping band can move relative to the housing when the crimping band is radially aligned with the actuation portion of the band opening, and wherein the housing restricts relative movement between the crimping band and the housing when the crimping band is radially aligned with the locking portion of the band opening.

7. The crimping device of claim 1, further comprising a locking mechanism coupled to the housing and configured to restrict relative movement between the crimping band and the housing.

8. The crimping device of claim 7, wherein the locking mechanism is disposed adjacent to the band opening of the housing.

9. The crimping device of claim 7, wherein the locking mechanism comprises a plurality of jaws, and wherein the jaws are movable between on open configuration spaced from the crimping band and a closed configuration contacting the crimping band.

10. The crimping device of claim 9, wherein the jaws comprise mating features configured to retain the jaws in the closed configuration.

11. The crimping device of claim 10, wherein the mating features of the jaws comprise interlocking tabs that extend from the jaws.

12. The crimping device of claim 1, wherein the crimping band comprises an indicator configured to signify to a user that the prosthetic heart valve is fully radially compressed.

13. The crimping device of claim 1, further comprising one or more stopper elements extending outwardly from the crimping band, wherein the one or more stopper elements are configured to restrict relative movement between the crimping band and the housing.

14. The crimping device of claim 1, wherein the crimping band has only one loop.

15. A crimping device for a mechanically expandable prosthetic heart valve, the crimping device comprising:
a housing comprising a base and a main body, wherein the main body extends from the base and comprises a lumen configured to receive the mechanically expandable prosthetic heart valve, the main body further comprising a first opening and a second opening, wherein the first opening and the second opening are spaced apart and extend from an inner surface of the main body that defines the lumen to an outer surface of the main body; and
a crimping band comprising a first end portion, a second end portion, and only a single loop disposed between the first and second end portions, wherein the single loop of the crimping band comprises a width that is less than an axial length of the mechanically expandable prosthetic heart valve.

16. The crimping device of claim 15, wherein the crimping band is a flexible polymeric band.

17. The crimping device of claim 15, wherein the crimping band is a flexible suture.

18. The crimping device of claim 15, wherein the crimping band is a flexible wire.

19. A crimping device comprising:
a housing having a lumen configured to receive a prosthetic heart valve; and
a crimping band adjustably coupled to the housing and comprising a first end portion, a second end portion, and a loop, wherein the loop of the crimping band is disposed within the lumen of the housing and can be moved between a first configuration and a second configuration, wherein in the first configuration, the loop of the crimping band has a first diameter and is configured such that the prosthetic heart valve in a radially expanded configuration can be positioned radially within the loop, wherein in the second configuration, the loop of the crimping band has a second diameter and is configured to apply a radial force on the prosthetic heart valve to move the prosthetic heart valve from the radially expanded configuration to a radially compressed configuration, and wherein the loop of the crimping band is configured to contact less than one half of an axial length of the prosthetic heart valve,
wherein the crimping band comprises an indicator configured to signify to a user that the prosthetic heart valve is fully radially compressed.

20. The crimping device of claim 19, wherein the loop of the crimping band is configured to contact less than one eighth of the axial length of the prosthetic heart valve.

* * * * *